United States Patent [19]

Krabbenhoft

[11] 4,346,249

[45] Aug. 24, 1982

[54] PREPARATION OF PARA-ISOPROPENYLPHENOL

[75] Inventor: Herman O. Krabbenhoft, Scotia, N.Y.

[73] Assignee: General Electric Company, Schenectady, N.Y.

[21] Appl. No.: 252,653

[22] Filed: Apr. 9, 1981

[51] Int. Cl.$^3$ .................... C07C 37/00; C07C 39/06
[52] U.S. Cl. ................................. 568/782; 568/781; 568/783
[58] Field of Search ............... 568/781, 782, 740, 772, 568/783

[56] References Cited

U.S. PATENT DOCUMENTS

| | | | |
|---|---|---|---|
| 3,418,381 | 12/1968 | Jennings et al. | 568/781 |
| 3,953,526 | 4/1976 | Rosenthal | 568/772 |
| 3,957,897 | 5/1976 | Vrieland et al. | 568/782 |

OTHER PUBLICATIONS

Corson et al., "J. Organic Chem." vol. 23, (1958) pp. 544–549.

*Primary Examiner*—Werren B. Lone
*Attorney, Agent, or Firm*—Joseph T. Cohen; James C. Davis, Jr.

[57] ABSTRACT

Para-isopropenylphenol can be obtained by dehydrogenation of para-isopropylphenol in the presence of a calcium-nickel phosphate catalyst, phenol, and water.

3 Claims, No Drawings

PREPARATION OF PARA-ISOPROPENYLPHENOL

This invention is concerned with a process for preparing para-isopropenylphenol. More particularly, the invention relates to a method for preparing para-isopropenylphenol from para-isopropylphenol by passing the para-isopropylphenol over a catalyst bed comprising essentially a calcium-nickel phosphate catalyst at elevated temperatures in the presence of phenol and water.

Para-isopropenylphenol has many uses. Among such uses are in the synthesis of 2,2-bis-(para-hydroxyphenyl)propane, also known as "bisphenol-A", as a comonomer for polymerizing with other olefinic materials such as copolymerization of paraisopropenylphenol with styrene, methyl methacrylate, etc.; and as an antioxidant.

Several methods have been described in the literature for the preparation of para-isopropenylphenol, including the catalytic dehydrogenation of para-isopropylphenol with catalysts composed of a mixture of chromium oxide and aluminum oxide, or a catalyst mixture comprising magnesium oxide, iron oxide, copper oxide, and potassium oxide. A more complicated process for preparation of the isopropenylphenol involves the reaction of a methyl Grignard reagent with para-hydroxyacetophenone or methyl para-hydroxybenzoate followed by dehydration. Although the above methods for dehydrogenation or preparation of paraisopropenylphenol have worked to some degree, the usual dehydrogenation catalyst called for the purpose have not given the rate of conversion to para-isopropenylphenol which is required for commercial use. Moreover the Grignard reaction is highly complicated and expensive and is again not a practical way of making para-isopropenylphenol.

I have now discovered that a certain catalyst, namely a calcium-nickel phosphate catalyst is exceptionally appropriate for dehydrogenating the para-isopropylphenol (hereinafter referred to as "propylphenol") to the corresponding para-isopropenylphenol (hereinafter designated as "propenylphenol") whereby much better conversion to the desired product for shorter periods of time is possible than by means of catalysts heretofore employed for dehydrogenation of the propylphenol to the propenylphenol.

The use of a calcium-nickel phosphate catalyst for dehydrogenation has been known in the past and has generally been used for dehydrogenating either saturated aliphatic compounds to introduce unsaturation into the compounds or to dehydrogenate olefinic compounds to introduce another olefinic linkage, as, for instance, in the making of compounds, such as isobutylene and butadiene. U.S. Pat. No. 3,935,126—Vrieland describes the dehydrogenatin of alkyl aromatic compounds free of nuclearly bound hydroxy groups in the para position using a calcium-nickel phosphate catalyst. However, it should be emphasized that, on account of the well known resonance interaction between a hydroxyl group and an alkenyl group (when they are attached to an aromatic nucleus in a para or 1,4-relationship), which tends to render the desired product, para-isopropenylphenol, in this case, highly susceptible toward decomposition under the same conditions as its formation when done so by catalytic dehydrogenation, the usual dehydrogenation (and/or oxydehydrogenation), catalysts and processes would have been expected to be ineffective for the efficient production of para-isopropenylphenol from para-isopropylphenol.

The situation described above for para-alkenylphenols (such as para-isopropenylphenol) should be contrasted to that encountered in the dehydrogenation of meta-alkylphenols (such as the meta-ethylphenol mentioned in the aforesaid U.S. Pat. No. 3,935,126) which on account of the inability of the alkenyl group and the hydroxyl group to interact via resonance when attached to an aromatic nucleus in a meta or 1,3-relationship are generally stable to the usual catalytic dehydrogenation conditions employed for their production.

Consequently, it was entirely unexpected and in no way could have been predicted that the calcium-nickel phosphate catalyst, in combination with the phenol and water, would have given the exceptional conversion results when contrasted with prior art dehydrogenation catalysts. For instance, iron oxide based catalysts have been used for dehydrogenation purposes (including the conversion of isopropylbenzene to isopropenylbenzene), but when such dehydrogenation catalysts are used to dehydrogenate para-isopropylphenol, conversions to the desired para-isopropenylphenol of the order of only 3% are obtained. Similar deficiencies are found when still other dehydrogenation catalysts are employed in combination with para-isopropylphenol, such as catalysts based on mixtures of (1) chromium oxide and aluminum oxide, or (2) magnesium oxide, iron oxide, copper oxide, and potassiun oxide, wherein the use of the latter dehydrogenation catalysts fails to produce any of the desired para-isopropenylphenol from para-isopropylphenol. In addition, there is no indication in the aforementioned U.S. Pat. No. 3,935,126 that para-isopropylphenol can be dehydrogenated over a calcium-nickel phosphate catalyst to provide para-isopropenylphenol, nor did the patentee use, as the applicant does, with the catalyst a mixture of phenol and water to obtain the desired results described herein.

To realize the maximum impact of this particular catalyst for the intended purpose, in addition to the isopropylphenol being passed over the catalyst bed at elevated temperatures, one also mixes with the propylphenol both water and phenol. The water acts as a decoking agent and contributes to the life of the catalyst. The phenol acts to prevent or greatly retard dealkylation reactions which might occur with alkylphenols (such as para-isopropylphenol) and alkenylphenols under the usual dehydrogenation reaction conditions by shifting the chemical equilibria in favor of the alkylphenol and alkenyl phenol. Thus, using the claimed dehydrogenation process, selectivities of 90% or higher have been achieved for the conversion of the isopropylphenol to the isopropenylphenol. These results may be compared to the 64.4% selectivity stated for the conversion of the meta-substituted (3-ethylphenol) to 3-vinylphenol referred to in the aforesaid U.S. Pat. No. 3,935,126.

The amount of phenol or water used with the propylphenol is not critical and can be varied widely. Thus, for each mol of propylphenol employed, one can use from 0.5 to 5 mols of phenol and from 0.5 to 4 mols of the water.

The calcium-nickel phosphate (referred to as "catalyst") can be prepared in various ways. Normally, the catalyst comprises a normal metal phosphate material consisting of phosphate radicals chemically combined with calcium and nickel in a molar ratio of calcium of from 6.5 to 12, preferably from 7.5 to 9.2 atoms of calcium per atom of nickel, the total amount of calcium and nickel being sufficient to satisfy the valences of the phosphate radical. One method is to form a mixture of calcium and nickel salts with a water-soluble orthophosphate whereby the calcium nickel phosphate is formed as a suspension of small particles. Methods for preparing the catalyst may be found, for instance, in U.S. Pat. No. 3,542,813 issued Feb. 20, 1951; U.S. Pat. No. 2,816,081 issued Dec. 10, 1957, U.S. Pat. No. 2,442,320 issued May 25, 1948; U.S. Pat. No. 2,824,843 issued Feb. 25, 1957; U.S. Pat. No. 3,935,126 issued Jan. 27, 1976; U.S. Pat. No. 2,971,035 issued Feb. 7, 1961; and in the article in *Industrial and Engineering Chemistry*, 43 2871-2874—Britton et al. published December, 1951. By reference, these patents and article are made part of the disclosures and teachings of the instant application as means for describing and making the nickel-calcium phosphate catalyst.

In the practice of the invention, a reaction tube, usually a quartz reaction tube, is packed with the catalyst which can have the formula:

$$Ca_8Ni(PO_4)_6, \qquad \text{I.}$$

although the molecular configuration of the catalyst is not limited to this particular formula. Before use, the catalyst is advantageously calcined at elevated temperatures in the range of from 600°–800° C. to remove any ingredients used in the preparation of the catalyst, such as graphite to facilitate pelletizing the catalyst for its intended purpose. This calcining can take place for a period of time ranging from 5–20 hours.

The temperature of reaction at which passage of the propylphenol over the catalyst bed is carried out is not undesirably critical and can be varied widely; usually temperatures above 275° C. but below the decomposition point of any of the reactants or reaction products are employed. Generally, the temperature can advantageously range from 300°–500° C. A simultaneous air flow, the rate of which is not critical, is also desirable with the passage of the propylphenol and can be at a rate of approximately 0.05 to about 3 cubic feet per hour, advantageously at atmospheric pressure, although superatmospheric pressure is not ruled out.

In order that those skilled in the art may better understand how the present invention may be practiced, the following example is given by way of illustration and not by way of limitation. All parts are by weight, unless otherwise indicated.

EXAMPLE 1

A quartz tube 40 cm×16 mm, inside diameter, with Vigreux indentations 1" above the top of the bottom joint was packed with 3 cm of quartz rings, 28 cm (equivalent to 44.16 grams) of the calcium-nickel phosphate catalyst of formula I, which had previously been calcined at about 800° for a period of 17 hours and then filled with additional quartz rings (for heat transfer). Thermocouples were placed on the side of the tube and the tube placed in a vertical furnace. At the top of the tube was placed a manifold from which the air and liquid feeds were added. At the bottom of the tube were placed in series three three-necked flasks, the first two being immersed in ice/water baths. The catalyst bed was heated to a temperature between 300°–500° with an air flow of 0.15 ft³/hr. Then the liquid feed composed of phenol, water, and isopropylphenol in the molar ratio of 2.8:2.0:1.0 was introduced to provide an addition rate of 0.15 ml/min. After specified volumes of feed had been introduced, the products (phenol, water, the propylphenol and propenylphenol) were collected from the receiver and analyzed for para-isopropenylphenol content by NHMR spectroscopy (proton nuclear magnetic resonance). Table I shows the results of para-isopropenylphenol formation as a function of the moles of para-isopropylphenol used.

TABLE I

| Cut | 1 | 2 | 3 | 4 | 5 | 6 | 7 | 8 | 9 | 10 |
|---|---|---|---|---|---|---|---|---|---|---|
| $X_{IPP}$ | 0.36 | 0.52 | 0.58 | 0.61 | 0.61 | 0.62 | 0.59 | 0.57 | 0.57 | 0.58 |

The item "Cut" was taken after each additional five ml increment of feed supplied to the reaction column. $X_{IPP}$ constituted the mole fraction of para-isopropenylphenol (IPP) relative to that of para-isopropylphenol (ipp); i.e., $$X_{IPP} = \frac{\text{moles } IPP}{\text{moles } IPP + \text{moles } ipp}$$

As can be seen from the above-identified Table I, the conversion is approximately 60% throughout the duration of the tests. The actual conversion is probably slightly less since tests have shown that phenol is also produced in an amount of 5% as a result of dealkylation of the p-isopropylphenol and probably also the isopropenylphenol. This is a considerable improvement over that observed with a variety of other catalysts used for the dehydrogenation of the propylphenol as a result of prior work which has been done in this field.

Although good results were obtained, using the catalyst in the manner described in Example 1, it was found that the catalyst tended to become inactive if it was allowed to remain in a standby condition between runs conducted over the same catalyst bed. It was discovered that by heating the catalyst (after about 18 hours standby) to about 800° C. for about 3–5 hours, this resulted in reactivation of the catalyst to almost its former activity. The following Table II shows the results obtained by passing the isopropylphenol over the reactivated catalyst bed (in the manner described above) under essentially the same conditions as was done in Example 1, with the exception that the cut was taken after each additional 10 ml increment (instead of 5 ml increment) of feed supplied to the column, except for cut No. 1 which was about 2 ml and Nos. 4 and 5 which were about 5 ml each.

TABLE II

| Cut | 1 | 2 | 3 | 4 | 5 | 6 | 7 | 8 |
|---|---|---|---|---|---|---|---|---|
| $X_{IPP}$ | 0.14 | 0.43 | .52 | .53 | .38 | .50 | .39 | .14 |

The results were obtained after about an 18 hour (inaction) standby. The $X_{IPP}$ were derived in the same manner as described in Table I.

As can be seen from Table II, the conversions were nearly as high in some instances as those obtained with the so-called "virgin" or first catalyst bed. Significantly, the catalyst did not become deactivated upon being left in the standby condition overnight or for a period of about 17 to 18 hours. After a total passage of about 62 ml., the catalyst did become deactivated again. Fortunately, the catalyst could be reactivated by heating at 800° C. overnight as shown in Table III which summarizes the results obtained after the second regeneration of the catalyst.

TABLE III

| Cut | 1 | 2 | 3 | 4 | 5 | 6 | 7 |
|---|---|---|---|---|---|---|---|
| $X_{IPP}$ | .19 | .39 | .51 | .48 | .54 | .38 | 0.00 |

Although the catalyst again became deactivated after a period of usage, it could have been reactivated again as described above.

It will of course be apparent to those skilled in the art that in addition to the calcium-nickel phosphate catalyst employed in the foregoing examples other calcium-nickel phosphate catalysts can be employed, many examples of which have been given in the aforesaid patents and article, without departing from the scope of the invention. Additionally, the conditions of reaction and procedures may be varied widely within the intended scope of the claimed invention.

What I claim as new and desire to obtain by Letters Patent of the United States is:

1. The process for making p-isopropenylphenol which comprises passing p-isopropylphenol, in combination with phenol and water, over a calcium-nickel-phosphate catalyst bed at a temperature of 275°–500° C., wherein the calcium-nickel-phosphate catalyst is calcined at a temperature of from 600°–800° C. prior to its use as the catalyst in the reaction, there being employed for each mol of the p-isopropylphenol, from 0.5 to 5 mols of phenol and 0.5 to 4 mols of water.

2. The process as in claim 1 wherein the calcium-nickel phosphate catalyst has a nominal formula:

$Ca_8Ni(PO_4)_6$.

3. The process as in claim 1 wherein after passage of the p-isopropylphenol over the catalyst bed, the catalyst is reactivated by heating at elevated temperatures.

* * * * *